United States Patent [19]

Emmons et al.

[11] Patent Number: 5,047,322

[45] Date of Patent: Sep. 10, 1991

[54] USE OF DRY ANALYTICAL ELEMENTS TO DETERMINE ANALYTES

[75] Inventors: Robert E. Emmons, Victor; Linda A. Mauck; John C. Mauck, both of Rochester, all of N.Y.; TaiWing Wu, Toronto, Canada; Royden N. Rand, Pittsford, N.Y.; Angelo P. Andrese, West Chester, Pa.

[73] Assignee: Eastman Kodak Company, Rochester, N.Y.

[21] Appl. No.: 251,494

[22] Filed: Sep. 30, 1988

Related U.S. Application Data

[63] Continuation-in-part of Ser. No. 68,767, Jun. 29, 1987, abandoned, which is a continuation-in-part of Ser. No. 811,031, Dec. 19, 1985, abandoned.

[51] Int. Cl.$^5$ .................... C12Q 1/68; G01N 33/561
[52] U.S. Cl. .................................. 435/6; 422/57; 422/58; 435/7.1; 435/7.4; 435/7.92; 435/17; 435/26; 436/515; 436/516
[58] Field of Search .................. 435/7, 6, 7.1, 7.4, 435/7.92, 17, 26; 436/810, 515, 516

[56] References Cited

U.S. PATENT DOCUMENTS

| | | |
|---|---|---|
| 3,975,162 | 8/1976 | Renn . |
| 4,130,471 | 12/1978 | Frosch . |
| 4,144,306 | 3/1979 | Figueras .............................. 422/56 |
| 4,246,084 | 1/1981 | Gurske . |
| 4,455,370 | 6/1984 | Bartlesman et al. .................... 435/6 |

FOREIGN PATENT DOCUMENTS 1048910 10/1976 Canada .
1072428 10/1978 Canada .
230762 5/1987 European Pat. Off. .

OTHER PUBLICATIONS

Mickle et al, *Clin. Chem.* 24 (4), pp. 698–700 (1978) "Improved Technique for Developing Creatine Kinase Isoenzyme Bands by Using a Substrate in Gelatin Matrix".
1984–1985 Enzyme Systems Products Expanding Catalog.
Smith, *J. Histochem. Cytochem.*, 32 (12), pp. 1265–1274 (1984) "Identification of Protease Isozymes after Analytical Isoelectric Focusing Using Fluorogenic Substrates Impregnated into Cellulose Membranes".

*Primary Examiner*—Sam Rosen
*Attorney, Agent, or Firm*—Dana M. Schmidt

[57] ABSTRACT

Dry transparent analytical elements can be used to determine analytes which have been separated by electrically induced migration through a solid medium, e.g. by electrophoresis, or which are intracellular enzymes. The dry transparent element is placed on a plate containing the analytes, and kept there until the analytes have reacted to produce a non-diffusible detectable species solely in the element. The element is removed and the detectable species is evaluated therein. The elements contain a water-insoluble binder material having an interactive composition dispersed therein which reacts with analyte to produce the non-diffusible species. The same electrophoretic plate can be used to successively determine the same or a plurality of analytes since it is not altered or destroyed by contact with the dry element.

28 Claims, No Drawings

USE OF DRY ANALYTICAL ELEMENTS TO DETERMINE ANALYTES

RELATED APPLICATIONS

This is a continuation-in-part of application Ser. No. 068,767, filed on Jun. 29, 1987, which is a continuation-in-part of Ser. No. 811,031, filed on Dec. 19, 1985, both now abandoned.

FIELD OF THE INVENTION

This invention relates to bioanalysis. For example, it relates to a method for determining analytes which have been separated electrically, e.g. by electrophoresis. It also relates to a kit useful in this method.

BACKGROUND OF THE INVENTION

A variety of analytical procedures have been developed for the separation and identification of different molecular species present in a specimen. Separation is generally accomplished by applying the specimen to a water-containing solid medium and inducing molecular separation of the species within the medium. In particular, chromatography and electrophoresis have been employed, both of which provide separation of different molecular species. The separation medium is generally called a chromatographic medium or electrophoretic plate. In such processes, a variety of reagents which interact with one or more of the molecular species in the specimen may also be applied to the medium before, during or after the separation process to assist in separation or identification of the analytes.

In general, poor resolution inhibits identification of separated materials in conventional electrophoretic media because of gross diffusion of the water-soluble reagents in the medium due to the presence of water. Proteins can be fixed to the medium with an acid or solvent to give quite sharp signals when stained. However, the fixing process usually destroys enzyme activity by denaturation. Further, the stains do not generally have the same affinity for all proteins to be determined.

Reagents have been introduced into the electrophoretic medium by a number of means. For example, U.S. Pat. No. 3,975,162 (issued Aug. 17, 1976 to Renn) describes the use of a transfer device composed of water-soluble reagents dispersed in a water-soluble binder. When the wetted device is placed on the surface of an electrophoretic plate, the binder dissolves and the water-soluble reagents diffuse into the plate to react with the separated analytes. This technique has a number of disadvantages. The electrophoretic plate can be used only once because the reagents diffuse in water and the resulting detectable signal is observed in the plate. Moreover, because reagent transfer is carried out in highly aqueous environment, resolution of the resulting analyte-reagent signals is poor. The reaction product (e.g. dyes) tends to spread out in the medium due to capillary action. Further, the procedure can be difficult to carry out.

U.S. Pat. No. 4,455,370 (issued June 19, 1984 to Bartelsman et al) describes the use of a microporous nylon membrane to transfer analytes, e.g. nucleic acids, from an electrophoretic plate to the membrane by electroblotting. All analytes are transferred since the membrane has limited selectivity. The membrane is then treated to provide a detectable signal in the presence of analytes. It does not contain reagents which provide a detection means. Further the transfer process is carried out in an aqueous environment.

Cellulosic membranes impregnated with water-soluble fluorogenic substrates have been described for use for identifying isoenzymes in an electrophoretic plate by R. E. Smith, in *J. Histochem. Cytochem.*, 32(12), pp. 1265-1274 (1984). Smith claims that his membrane overlay provides highly resolved identification bands. However, these membranes have a number of serious drawbacks. The membrane overlay must be wet when used. As a result, the identification bands are quite diffuse because the substrates which provide a detectable signal are water-soluble. Further, the overlays do not provide a means for multiple testing with the same electrophoretic plate because substrate diffuses into the plate from the overlay. In essence, the Smith overlay can be used in a single test only.

The Smith overlay membranes are not transparent and are therefore limited in utility. They cannot be used for transmission analysis using colorimetric detection procedures.

It would be useful to have a means for overcoming the problems noted above. In particular, it would be desirable to have a means for detecting a plurality of electrically separated analytes using the same electrophoretic plate. It would also be useful to be able to use either colorimetric or fluorometric signals for detecting analytes.

SUMMARY OF THE INVENTION

The present invention provides a solution to the problems encountered with known electrophoretic detection procedures with a method for determining an analyte comprising the steps of:

A. forming a laminate by overlaying a plate adapted for electrically induced migration and containing a plurality of analytes which have been separated from one another electrically with an analytical element containing a water-insoluble binder material having dispersed therein an interactive composition which will react with at least one of the analytes to provide a non-diffusible detectable species solely in the element, and B. removing the element from the plate and determining the detectable species in the element.

In particular, the present invention provides a means to identify one or more analytes separated electrically using the same electrophoretic plate. In other words, this invention provides a multitest detection procedure. The method of this invention is easy to use, relatively inexpensive and highly sensitive. In preferred embodiments, it can be used with either colorimetric or fluorimetric detectable species.

These advantages are achieved by using as an overlay an anlytical element containing a water-insoluble binder material having reagents dispersed therein which will react with the analyte of interest to provide a non-diffusible detectable species. Analyte reaction occurs at the interface of the plate and overlay to give very definitive bands. Since the detectable species is non-diffusible in water, it does not migrate from the overlay to the plate. Therefore, the same plate can be used repeatedly in an unlimited number of successive tests to determine one or more analytes.

Further, the assay is carried out under substantially dry conditions thereby minimizing the diffusion of the bands in the overlay, and the conditions encountered with known methods which reduce their sensitivity.

In another aspect of the invention, such an overlay is used to detect intracellular enzymes of cells. The steps are disposing such cells on a support, and overlaying the support with a dry, transparent element comprising a water-insoluble binder and an interactive composition capable of reacting with at least one of the enzymes to produce a detectable change, the interactive composition further including a surfactant of the type and in an amount effective to induce leakage of at least one enzyme out of the cells.

DESCRIPTION OF THE PREFERRED EMBODIMENTS

The present invention can be used to advantage in various fields of study including medicine, immunology, genetics, microbiology, biochemistry, clinical chemistry and forensic science to name a few. Any substance which can be electrically induced to migrate through an aqueous medium and be separated from other substrances on the basis of molecular charge can be identified using this invention. Such substances are described herein as "analytes". For example, this invention can be used for diagnostic purposes for detection of specific enzymes, antigens or antibodies in biological fluids, e.g. blood. In forensic science, it can be used in the phenotyping of genetic variants of enzymes and other proteins for the purpose of identification of individualization. Analyses of nucleic acids, peptides and other cellular components are also possible. In a preferred embodiment, the invention is useful for determinations of various proteins, such as enzymes (e.g. creatine kinase, lactate dehydrogenase, alkaline phosphotase, glucose-6-phosphate dehydrogenase, adenylate kinase, $\gamma$-glutamyl trasferase, peroxidase, etc.). In a first preferred embodiment, the presence of isoenzymes that have been separated into discrete bands can be determined to advantage with this invention, including the presence of isoenzymes of creatine kinase, alkaline phosphotase and lactate dehydrogenase. In a second preferred embodiment, enzymes are detectable as labels on antibodies specific to the analyte, or to an antibody to the analyte. Such antibodies can be reacted with the analyte before or after electrophoretic separation of the analyte of choice from other proteins. In a third preferred embodiment, intracellular enzymes in live cells are detectable by using the overlay of this invention. It has been discovered that certain surfactants in the overlay are effective in inducing the cells to leak such enzymes out through the cell walls.

A plurality of analytes are generally present in an aqueous liquid, such as a human or animal biological fluid. In one embodiment of the invention, the analytes can be separated by electrically inducing migration in a solid medium. A suitable sample of that liquid is applied to a suitable medium used in molecular migration of affinity separation procedures induced electrically. Such media include electrophoretic plates and electrofocusing plates. There are many commerically available plates which can be used in the method of this invention including those described, for example, in U.S. Pat. No. 3,975,162 (noted above) and those shown in the examples below. Generally, such plates have one or more compartments in a thin layer of a hydrated gel or membrane. Particularly useful are the plates prepared from hydrated gels, such as agarose, agar, polyacrylamide, acrylamide, and others known in the art. The agarose and polyacrylamide plates are preferred in the practice of this invention.

Once the liquid sample has been applied to the plate, it is subjected to a suitable electrical current to induce molecular migration and separation of the analytes, one from another. Known separation procedures can be used. For example, electrophoresis can be used whereby the analytes are subjected to an electrical field at constant pH and ionic strength. Another separation technique is electrofocusing whereby molecules are subjected to a pH gradient and separated on the basis of their individual isoelectric points.

After molecular separation has proceeded to a suitable extent, the surface of the electrophoretic plate is placed in contact with an analytical element (described below) in a manner that insures a minimum number of air bubbles at the interface. Generally, a laminate of the plate and element is formed by overlaying the plate with the element. The surface of the element and the surface of the plate which are in contact form an interface at which reaction of analyte and interactive composition (described below) can occur. Since there is relatively little moisture present in this laminate, there is substantially no diffusion of analyte or non-diffusible detectable species across the interface. In other words, substantially no analyte leaves the plate and substantially no detectable species leaves the analytical element in the practice of this invention. This is attributable to the absence of a significant amount of water in either component of the plate-element laminate and the water-insolubility of the detectable species. There is minimal moisture in conventional electrophoretic plates, but the amount is not sufficient to cause migration of water-insoluble reagents in the element.

The element and plate are kept together for a time sufficient to allow reaction of analyte and interactive composition to provide a detectable species solely in the element. This time of reaction will vary depending upon the analyte, the interactive composition used and the concentration of the analyte and composition. A minimal amount of routine experimentation may be needed to find the optimum time for reaction. The reaction is preferably carried out at about 37° C. in an incubation step, although any temperature up to about 45° C. can be used.

The detectable species produced as a result of the reaction will depend upon the type of interactive composition employed in the element. Generally, the species is detectable by spectrophotometric means. That is, the species can be measured with an increase or decrease in colorimetric, fluorometric, chemiluminescent or phosphorescent density which is detectable with suitable detection equipment and procedures. Preferably, the element is transparent so that detectable chromogen is measured by transmission spectroscopy.

To determine the detectable species, the element is removed from the plate and subjected to appropriate detection procedures. If necessary, the element may be subjected to additional reagents or incubation to enhance the signal resulting from the species.

In another embodiment of the invention, intracellular enzymes, that is, those within live cells on a suitable support, are detected by the overlay of this invention. A wide variety of enzymes is so detectable, for example, creatine kinase (CK), alkaline phosphotase, lactate dehydrogenase (LD), peroxidase and esterase of which CK, alkaline phosphotase and LD are preferred examples. The enzymes are detectable because of their leakage caused by a surfactant of the overlay. Such detection is useful in toxicology, experimental biology, diagnostic medicine, determination of cell maturity and transformations, among other. For example, with appropriate controls dose related toxic insult on specific cell types can be evaluated via enzymatic activity. In another example, types of Leukemia (i.e. acute mylocytic, acute myelo-monocytic, acute monocytic, acute lymphocytic and erythroid) are commonly at least partially identified by the presence and/or degree of peroxidase and esterase activity.

In this process, the cells can be prepared for detection by any suitable process. For example, they can be washed before and/or after they are deposited on a glass slide, using normal saline as the wash liquid, and the overlay deposited on them. Alternatively, the enzymes of the cells can be detected while the cells are still on a culture medium such as agar, or the cells can be dropwise deposited directly on the element of this invention. In the case of direct, dropwise deposition, the cells are preferably washed first to remove any serum or culture media that might be coating them.

The overlay is similar to that described for the electrophoresis detection, except that the binder is preferably a hardened gelatin in each case. The surfactant is selected depending upon the enzyme to be detected. Any surfactant that will induce enzyme leakage, and still be compatible with the color production of the overlay in response to the presence of the enzyme, is useful. The preferred surfactants, located in the upper layer, and their amounts, are as follows, where "square meter" refers to the surface area of the upper coating of the overlay:

| Enzymes to be Detected | Type of Surfactant | Preferred Examples* | Amounts |
| --- | --- | --- | --- |
| creatine kinase | sodium salt of alkylaryl polyether sulfonate | Triton X200E manufactured by Rohm & Haas | 0.01 to 5 g/sq meter |
| creatine kinase | sodium alkyl napthalene sulfonate | Alkanol XC manufactured by DuPont | 0.05 to 1 g/sq meter |
| alkaline phosphotase | octylphenoxy polyethoxy ethanol | Triton X102E manufactured by Rohm & Haas | 0.5 to 3 g/sq meter |
| lactate dehydrogenase (LD) | octylphenoxy polyethoxy ethanol | Triton X-100 manufactured by Rohm & Haas | 0.05 to 5 g/sq meter |

*It is anticipated that other specific surfactants within the noted general "type" will also work.

The analytical element used in the practice of this invention generally comprises one or more water-insoluble binder materials. The binder material and interactive composition dispersed therein are distributed throughout a zone which may be a coated self-supporting layer or a layer coated on a nonporous support. Elements of particular interest are those currently available from Eastman Kodak Co. (Rochester, New York, U.S.A.) under the trademark EKTACHEM Clinical Chemistry slides. Preferably, such elements are modified by removal of the outermost porous spreading layers. Representative elements are illustrated in the Examples provided below. Other useful analytical elements are described, with or without spreading layers, in U.S. Pat. No. 3,992,158 (issued Nov. 16, 1976 to Przybylowicz et al), U.S. Pat. No. 4,042,335 (issued Aug. 16, 1977 to Clement), U.S. Pat. No. 4,144,306 (issued Mar. 13, 1979 to Figueras), U.S. Pat. No. 4,259,001 (issued Mar. 24, 1981 to Pierce et al) and U.S. Pat. No. 4,430,436 (issued Feb. 7, 1984 to Koyama et al).

The elements generally comprise one or more zones or layers composed of one or more water-insoluble binder materials. It is essential that at least the outermost zone or layer of the element which will be contacted with the electrophoretic plate be composed of a water-insoluble binder material so that the element does not stick to the plate which may contain a minimal amount of water. Such a binder material is insoluble in water to an extent of less than 1% by weight being soluble at 20° C. Useful binder materials include fibrous materials, such as filter paper, woven fabric, fibrous fleece or matting. In preferred embodiments, non-fibrous materials are used, such as natural or synthetic colloids (e.g. gelatin, polysaccharides, and the like) which can be hardened to render them highly water-insoluble, acrylamide polymers, vinyl pyrrolidone polymers, cellulose esters, cellulose ethers, polyvinyl esters, vinyl acetals and the like. Hardened gelatin is a preferred binder material.

The element can have one or more reagent layers containing one or more or all components of the interactive composition therein. Other layers can be present if desired, including subbing layers, radiation-blocking layers, reflective layers, regitration layers, barrier layers, spreading layers, and the like as known by one skilled in the art. One layer may perform a multiplicity of functions, e.g. a spreading layer which is also a reagent layer. Preferably, the layers are carried on a suitable nonporous support which is usually a polymeric material, such as cellulose acetate, poly(ethylene terephthalate), a polycabonate or a polyvinyl compound such as polystyrene. A support of choice will be compatible with the intended mode of detection. Preferred supports are radiation-transmissive which transmit electromagnetic radiation of a wavelength within the range between about 200 and about 900 nm as well as radiation due to radioactivity. Preferred supports are also relatively thin, e.g. less than about 0.2 mm in thickness, in order to provide suitable flexibility for overlaying on an electrophoretic plate.

The interactive composition incorporated into the element will depend upon the analyte of interest. This invention is not intended to be limited in the scope of useful compositions which participate in one or more reactions to provide a non-diffusible detectable species in response to the analyte. A skilled worker in clinical chemistry would be able to determine a suitable composition for a particular analyte.

It is essential that the interactive composition provide non-diffusible species which can be detected in some manner in the element. In the context of this invention, the term "non-diffusible" means that the species is not able to diffuse out of the element nor move laterally within it to any appreciable extent. However, other components of the composition may be able to move within the element between zones or layers. Non-diffusibility is preferably attained with water-insoluble species. These water-insoluble species may be coated in organic solvents which solubilize the species for coating or immobilizing purpose. Examples of useful non-diffusible species are dyes formed from water-insoluble leuco dyes, e.g. the triarylimidazoles described in U.S. Pat. No. 4,089,747 (issued May 16, 1978 to Bruschi). Other useful non-diffusible species or their precursors are known to those having ordinary skill in the art.

Alternatively, the detectable species can be water-insoluble, but rendered non-diffusible in the element in a suitable fashion, such as with mordants or immobilizing binders. Such water-soluble species and immobilizing materials are numerous and known to one of ordinary skill in the art.

In a preferred embodiment of this invention, an analytical element designed to determine creatine kinase (CK) is used to separate and identify CK isoenzymes. One such element is described in described in Example 1 below. The interactive composition in that element includes peroxidase, α-glycerophosphate oxidase, a water-insoluble triarylimidazole leuco dye which is capable of providing a water-insoluble detectable dye in response to the reaction of the isoenzymes, adenosine diphosphate (an enzyme substrate), glycerol and glycerol kinase. These reagents can be located in the same or different layers of the element. Other creatine kinase interactive compositions are known in the art.

A significant advantage of the method of this invention is that it can be used to determine a plurality (identified as N herein) of analytes successively using a single electrophoretic plate and liquid sample. In this embodiment, the method comprising the steps of:

A. forming a laminate by overlaying the plate containing the plurality of analytes which have been separated from one another electrically with a first analytical element containing a water-soluble binder material having dispersed therein an interactive composition which will react with the first of the analytes to provide a first detectable species solely in the first element, B. removing the first element from the plate, and C. repeating steps A and B up to N-1 times, using in each repetition of steps A and B, said plate and a respectively different dry analytical element containing a water-insoluble binder material having dispersed therein a respective interactive composition which will react with the respective analyte to provide a respective detectable species solely in the respectively different element, provided that the interactive compositions of at least the first (N-1) determinations react with the respective analytes to provide respective nondiffusible detectable species.

The detectable species produced in each element in this embodiment can be measured immediately after the element is removed from the plate, or the element can be kept in an appropriate environment for measurement later.

The measurement of a plurality of analytes according to this embodiment is illustrated in Example 3 below.

Alternatively, in a series of determinations, the last determination can be made with a diffusible detectable species as long as the preceding determinations are made with a non-diffusible species. Because the detectable species produced in the last test is diffusible, it may migrate into the plate thereby contaminating it for further tests.

In yet another embodiment, the last two determinations of a series of determinations can be made with different diffusible interactive compositions in succession if the detectable species produced thereby are distinct and can be separately measured. For example, one test can produce a fluorometric signal while the second test can produce a colorimetric signal. These determinations, however, must follow one or more tests wherein non-diffusible interactive species are produced and measured.

The analytical element and a plate (electrophoretic or electrofocusing) adapted for electrically induced migration of an analyte can be obtained individually, or together as a diagnostic kit. More than one element may be included in the kit either for the same analyte or for different analytes.

In the examples below provided to illustrate the practice of the invention, the materials used therein were obtained as follows:

Polyacrylamide gel plates and agarose gels for isoelectrofocusing, sodium hydroxide, surface pH electrode reference electrolyte (AgCl) an ampholine (pH range 3.5-9.5) from LKB Produkter (Bromma, Sweden), Cellulose acetate electrophoresis plates, tris-barbital-sodium barbital buffer, alkaline phosphotase isoenzyme fluor reagent and creatine isoenzyme reagent from Helena Laboratories (Beaumont, Tex., U.S.A.), Polyacrylamide gradient gel plates from Separation Sciences, Inc. (Attleboro, Mass., U.S.A.), AMP, ADP, DAPP, Tris.HCl and Tris base from Sigma Company (St. Louis, Mo., U.S.A.), α-Glycerophosphate oxidase from Toyo Jozo (Shizuoka-keu, Japan), TRITON X-100, X-102 and X-200 E surfactants from Rohm and Haas (Philadelphia, Pa., U.S.A.), ALKANOL XC surfactant from DuPont (Wilmington, Del., U.S.A.), Magnesium acetate from Allied Chemical Corp. (Morristown, N.J., U.S.A.), Peroxidase from Miles Laboratories (Elkhart, Ind., U.S.A.), Kerosene from Fisher Scientific Company (Fair Lawn, N.J., U.S.A.), Buffers (pH 4 and 7) from Corning Science Products (Medfield, Mass., U.S.A.), Buffer (pH 10) from VWR Scientic, Inc. (San Francisco, Calif., U.S.A.), N-acetyl-L-cystein from Boehringer Mannheim GMBH (West Germany), and the remainder from Eastman Kodak Company (Rochester, N.Y., U.S.A.).

As used in the context of this disclosure, I.U. represents the International Unit for enzyme activity defined as one I.U. being the amount of enzyme activity required to catalyze the conversation of 1 micromole of substrate per minute under standard pH and temperature conditions for the enzyme.

METHODS

A. Electrophoretic methods of the prior art were performed according to procedures recommended by the manufacturers of the equipment used. Samples were spiked with 20 mmole of N-acetyl-L-cystein to enhance creatine kinase (CK) performance. N-acetyl-L-cystein was not present in the analytical element. Highlights of those methods are:

1. CK Electrophoresis Procedure, Helena Laboratories, Procedure No. 20, (dated 8/80). The isoenzymes of CK are separated according to their electrophoretic mobility on a cellulose acetate electrophoretic plate in a tris-barbital buffer. After separation, the cellulose acetate plates are laminated to a Helena CK Isoenzyme Reagent substrate overlay and incubated at 37°-40° C.

At the end of the incubation period (25-30 minutes), the laminated materials were separated and the stained cellulose acetate plates were completely dried in an incubator.

The resulting CK bands on the stained cellulose acetate plate were visualized using UV lamp or quantitated in a densitometer using either visible light or ultraviolet light and fluorescence quenching.

2. Analytical Electrofocusing in Polyacrylamide Gel (PAG):

| Ampholyte | Compositions | |
|---|---|---|
| PAG Plates | pH 3.5-9.5 | pH 5.5-8.5 |
| Anode Electrode Solution buffer | 1 Molar H₃PO₄ | 0.4 Molar HEPES buffer |
| Cathode Electrode Solution | 1 Molar NaOH | 0.1 Molar NaOH |
| Cooling | 10° C. | 10° C. |
| Power Supply Settings | Power = 30 Watts Voltage = 1800 Current = Maximum | Power = 30 Watts Voltage = 1800 Current = Maximum |
| Time | 1.5 Hours | 2.5 Hours |

3. Analytical Electrofocusing (EF) in Agarose:

| Analytical | Compositions | |
|---|---|---|
| EF in Agarose | pH 3.5-9.5 | pH 5.0-8.0 |
| Anode Electrode Solution buffer | 0.5 Molar Acetic Acid | 0.04 Molar L-Glutamic Acid |
| Cathode Electrode Solution | 0.5 Molar NaOH | 0.5 Molar NaOH |
| Cooling | 10° C. | 10° C. |
| Power Supply Settings | Voltage = Maximum Current = Maximum Power = Initially zero, then increase until 500 V is attained* | Voltage = Maximum Current = Maximum Power = Initially zero, then increase until 500 V is attained* |
| Time | 30 Minutes | 30 Minutes |

*Setting electrical parameters in this manner enables one to use the recommended settings for any sized gel.

B. Electrofocusing was carried out in the following manner.

1. The cooling plate of the Multiphor was coated with kerosene.
2. The template was laid on the cooling plate and any air bubbles were removed.
3. The template was coated with kerosene.
4. The agarose gel was laid on top of the template with the plastic side downward to avoid trapping air bubbles.
5. The electrode strips were evenly saturated with the appropriate electrode solutions. A faint trail of moisture remained on the toil if the strips were properly wetted. Any excess solution was removed by blotting.
6. The wicks were laid as straight as possible, on the proper position as indicated by the template.
7. The wicks were cut sharply just short of the edge of the gel.
8. The samples were applied as desired, avoiding the edges of the gel. The sample volume was 15-20 $\mu$l. Small volumes (e.g. 2 $\mu$l) were directly pipetted onto the gel surface. For most proteins, the best application site is 2-4 cm from the cathode strip. High-molecular-weight proteins were applied close to their expected pI positions.
9. The electrofocusing lid for focusing across the gel was applied, the electrode wires were aligned along the electrode strips, and the red and black wires were connected.
10. The pressure bar (not needed for gels with pH 3.5-9.5 range ampholytes) was inserted into the safety lid, and the lid was placed in position.
11. The power supply was turned on.
12. After 20-30 minutes of focusing, the power was turned off and the sample application pieces were removed. The lids were replaced and focusing continued at the same power settings.

EXAMPLE 1

Determination of Creatine Kinase (CK) Isoenzymes—A Comparison of Present Invention with A Known Method A repeating series of serum samples was applied to a polyacrylamide gel plate containing ampholytes in the pH range of 3.5-9.5. The samples were electrofocused for 90 minutes according to the procedure described above. Following this, the plate was cut in half and excess moisture removed. To one half, a modified EK-TACHEM dry analytical element (described below) for the detection (visualization) of CK isoenzymes was applied according to the present invention. To the other half, a warm substrate-dye, agarose solution was overlayed and allowed to cool to form a Control electrophoretic plate-overlay laminate. Both halves were placed in an incubator and allowed to react for the same length of time at 37° C.

Both overlays were removed from the respective PAG plates. Upon observation, the bands on the dry analytical element used in this invention were clearly defined whereas those on the agarose overlay (Control) were diffuse and poorly defined. Moreover, bands were evident on the Control electrophoretic plate indicating that diffusion occurs from the overlay to the plate. No bands were evident on the plate used according to this invention.

The analytical element used for the determination of electrophoretically separated creatine kinase isoenzymes described above had the following format:

| | |
|---|---|
| Gelatin (hardened) | 2.0-10 g/m² |
| TRITON X-200E surfactant | 0.01-5 g/m² |
| Bis Tris Buffer* | 1.0-3 g/m² |
| Creatine Phosphate | 0.25-10 g/m² |
| Adenosine Diphosphate (ADP) | .02-2 g/m² |
| Adenosine Monophosphate (AMP) | 0.1-10 g/m² |
| Glycerol | .05-2 g/m² |
| Magnesium Acetate | 0.05-2 g/m² |
| Diadenosine Pentaphosphate (DAPP) | 0.001-0.55 g/m² |
| Glycerol Kinase | 400-8000 I.U./m² |
| Gelatin | 2.0-10 g/m² |
| Tris Buffer | 1.0-3 g/m² |
| Dimedone | 0.01-1 g/m² |
| 2-(3,5-dimethoxy-4-hydroxyphenyl)-4,5-bis(4-dimethylaminophenyl)-imidazole | .02-2 g/m² |
| 2-4-Di-n-pentylphenol | 0.5-10 g/m² |
| ALKANOL XC surfactant | 0.05-1 g/m² |
| TRITON X-200E surfactant | 0.01-5 g/m² |
| Glycolic Acid | 0.1-0.5 g/m² |
| Ascorbic acid oxidase | 5,000-15,000 I.U./m² |
| Peroxidase | 10,000-50,000 I.U./m² |
| $\alpha$-Glycerophosphate oxidase | 1,000-5,000 I.U./m² |
| Support | |

*Bis Tris = 2-bis(2-hydroxyethyl)amino-2-(hydroxymethyl)-1,3-propanediol

EXAMPLE 2

Creatine Kinase Isoenzyme Determination—Comparison of Method of Present Invention with Cellulose Acetate Electrophoresis Plate Method of Helena Laboratories Example 1 was repeated using the CK electrophoresis procedure of Helena Laboratories and the method of the present invention.

Two plates containing cellulose acetate medium were soaked in electrode buffer, blotted and identical serum samples applied to each. Both plates were placed in a standard Helena chamber prepared as outlined in the manufacturer's instructions. Following electrophoresis, the plates were removed and treated as follows:

1. One plate was laminated with a dry analytical element as described in Example 1 above. Bubbles were removed at the interface, and the laminate was incubated at 37° C.
2. The other plate was laminated with a second cellulose acetate plate that had been prepared by:
   a. Being soaked in electrode buffer and then blotted.
   b. Loaded with the substrate-dye solution by coating the cellulose acetate with the CK reagent and allowing it to absorb.

The resulting laminate was placed in the incubator at 37° C. to develop. At the end of a specified period of time, both laminates were removed from the incubator and the overlays stripped off the plates.

The bands on both the cellulose acetate overlay and its corresponding electrophoresis plate were not visible under normal room lighting. When dried and placed under ultra-violet light, both the overlay and the electrophoresis plate showed bands. The bands on the overlay were very weak compared to those on the plate. The bands were diffuse. This is because during electrophoresis and the drying process that follows, the dye is carried by capillary action through the cellulose acetate thereby smearing the bands.

In contrast the test according to this invention using the dry analytical element showed bands in normal room light. The corresponding electrophoresis plate showed no bands. When the element and the corresponding cellulose acetate electrophoresis plate were placed under ultra-violet light, the element showed bands that were quenched against the fluorescent background. No bands were seen on the cellulose acetate electrophoresis plate because reagents and reaction products did not diffuse into the electrophoresis plate from the element. The bands present on the element were broader than those seen after isoelectric focusing. This is because without the focusing effect of electrophoresis in a pH gradient, the CK isoenzymes tend to diffuse during separation in an electric field. Despite this, the dry element was still much sharper than the plate using a cellulose acetate overlay.

EXAMPLE 3

Multiple Analysis Using a Single Eclectrophoretic Plate

The CK element used was that described in Example 1.

The alkaline phosphotase (ALP) element used in this assay is shown below. Titanium dioxide was placed in the gel layer to provide a white background for the yellow dye generated during isoenzyme band development.

| Reagent Layer | Gelatin (hardened) | 10–50 g/m$^2$ |
|---|---|---|
| | Mg Chloride | .01–.05 g/m$^2$ |
| | p-Nitrophenyl Phosphate | 0.2–1 g/m$^2$ |
| | TRITON X-102 surfactant | 0.5–3 g/m$^2$ |
| | Tris(hydroxymethyl)aminomethane buffer (pH 8) | 1–5 g/m$^2$ |
| | Poly(styrene-co-N-vinylbenzyl-N,N-dimethylbenzylammonium chloride-co-divinylbenzene) | .1–5 g/m$^2$ |
| Reflective Gel Layer | TiO$_2$ | 10–50 g/m$^2$ |
| | Gelatin (hardened) | 10–50 g/m$^2$ |
| | Tris(hydroxymethyl)aminomethane buffer (pH 8) | 1–5 g/m$^2$ |
| Support | | |

Serum samples were applied to two polyacrylamide gel plates and electrophoresis separation was performed as described above.

To plate I, the ALP element was applied and incubated as described above for 3–5 minutes. This element overlay developed yellow bands characteristic of ALP reaction using this substrate. No bands developed in the gel plate because no appreciable dye diffusion occurred during the short time of reaction.

The second plate II was overlayed with the modified CK element described in Example 1. Similarly to Example 1, clear bands were evident in the overlay. No bands were developed in the gel plate.

A fresh set of elements were again overlayed on the same polyacrylamide gel plates. This time, however, the order of overlay was reversed. The CK element was applied to plate I and the ALP element to plate II. The resulting laminates were incubated and dried as described above.

Both elements developed bands characteristic in color and appearance to the analytes they were designed to detect. The electrophoresis gels showed no band formation in either case.

This example demonstrates the multitest capability of the present invention. Successive application of dry analytical elements to a single electrophoretic plate can be used to determine those analytes for which the elements are designed to detect.

EXAMPLE 4

Comparison of Present Invention with Method of the Prior Art

This example compares the method of the present invention to an analyte determination using an "Enzyme Overlay Membrane" described by R. E. Smith in *J. Histochem. Cytochem.*, 32 (12), pp. 1265–1274 (1984), described above.

Enzyme overlay membranes (EOMs) comprising substrate-impregnated cellulose acetate for the detection of trypsin isoenzymes, were purchased from Enzyme Systems Products (Livermore, Calif., U.S.A.). These membranes contain a fluorogenic trypsin substrate to detect isoenzyme activity patterns on agarose and polyacrylamide electrophoresis plates.

Isoelectric focusing was performed on 0.5 mm thick polyacrylamide gel plates using a LKB horizontal electrophoresis system at a pH range of 3.5–9.5. The electrofocusing temperature was maintained at 5° C. The power supply settings were: voltage=1800, power=20 watts, current=200 milliamps. Focusing was carried out for about 2.5 hours.

Patient serum samples suspected of having elevated trypsin activity were prepared as follows: (1) left in native state, (2) spiked with bicarbonate-buffered trypsin (pH 6.6) having a calculated activity in excess of 1000 I.U./1, (3) a trypsin-spiked sample diluted to 1:1 with buffer, (4) a trypsin-spiked sample diluted 3:1 with buffer.

Each serum sample was subjected to electrophoresis as described above. An EOM was dipped into a bath of distilled water to moisten it, and was carefully laid over each gel plate so that no air bubbles were entrapped. The resulting laminates were incubated for 10-30 minutes at 37° C. An ultraviolet (long-wave) lamp was used to monitor the reactions in each laminate. When optimal fluorescence was obtained, the overlays were peeled off while the plates were still moist. The membranes were allowed to dry. Observation of the membranes and gel plates revealed the following:

The first serum sample showed slight activity in both application areas of the plate, i.e. at pH 8.5 and at pH 4.0. A very light streak of diffuse fluorescence connected the areas of primary activity.

The trypsin-spiked sample showed primary activity in the same regions. However, activity in the region between the primary bands resolved into more well defined bands surrounded by diffuse fluorescence. Dilutions of the spiked sample showed decreasing fluorescence that approximately correlated with the expected decreasing activity. The fluorescence appears to be unaffected by the pH gradient of the isoelectric focusing gel in the trypsin assay evaluated.

In order to check for diffusion of fluorescent substrate into or onto the gel plates, a sheet of wet, untreated cellulose acetate was applied to a gel plate previously overlayed with an EOM. Observation of the dried cellulose acetate showed diffuse fluorescence in the areas of EOM-gel reactions.

The disadvantages of using the commercially available EOMs are evident: (1) the EOM must be wet to activate the substrate, causing unwanted diffusion of the soluble substrates, (2) upon multiple testing, subsequent overlays exhibited progressively less distinct bands, (3) substrates useful in routine clinical analyses of serum components are not available (4) the EOMs are not transparent and therefore cannot be used for direct or transmission spectrophotometry, and (5) they are relatively expensive.

The assay described above was compared to an assay carried out according to the present invention as described in Example 1 above. The present invention provided highly distinct bands in the dry element whereas the electrophoretic plate had no observable bands and could be reused.

EXAMPLE 5

Determination of Peroxidase Enzymes

An analytical element was prepared for the determination of electrophoretically-separated antigens bound to antibodies labeled with peroxidase enzyme. The overlay element had the following format:

| | |
|---|---|
| d-glucose | 1-20 g/m$^2$ |
| polyvinyl pyrrolidone (PVP K-90) | 0.60-15 g/m$^2$ |
| Gelatin (hardened) | 1-20 g/m$^2$ |
| 3-morpholinopropanesulfonic acid buffer | 0.5-10 g/m$^2$ |
| "TX-100" surfactant | 0.10-3 g/m$^2$ |
| "Alkanol XC" Surfactant | 0.10-3 g/m$^2$ |

| -continued | |
|---|---|
| coupler solvent | 0.30-5 g/m$^2$ |
| Dimedone | 0.10-1 g/m$^2$ |
| 2-(3,5-dimethoxy-4-hydroxyphenyl)-4,5-bis(4-dimethylamino phenyl) imidazole | 0.20-2 g/m$^2$ |
| Gelatin (hardened) | 0.5-20 g/m$^2$ |
| "TX 100" Surfactant | 0.01-2 g/m$^2$ |
| 3-morpholinopropanesulfonic acid buffer | 0.5-10 g/m$^2$ |
| Glucose oxidase | 0.01-2 g/m$^2$ |
| Support | |

EXAMPLE 6

Peroxidase—Labeled Antibody Determination

A plate containing cellulose acetate medium was soaked in electrode buffer, blotted, and serum sample applied. The plate was placed in a standard Helena chamber. Preparation and operation of the chamber for electrophoresis were carried out as outlined by the manufacturer's instructions.

Following electrophoresis, the plate was removed and, if appropriate, residual endogenous peroxidase activity was decreased by covering the plate area with 3.0% hydrogen peroxide in absolute methanol for five minutes at ambient temperature. (A range of 0.5 to 3.0% $H_2O_2$ is useful.) This was drained. The plate was then gently flooded with phosphate buffered saline (PBS), incubated for five minutes and drained. This was repeated with fresh PBS.

To help eliminate cross-reactivity, the plate was then covered with normal (that is, from a disease-free animal) serum from the same host as used for the second antibody described hereinafter (rabbit). This was diluted to 5% with PBS, incubated 10 minutes at ambient temperature, and drained without washing.

The plate was then covered with the following as the primary antibody: "Affini Pure" Goat Anti-human $I_gG$ (H&L), diluted in the range of 1:200, using PBS. (A range of 1:100 to 1:200 is useful.) (All of the antibodies listed herein were obtained from Jackson Immuno Research Labs.) This was incubated 30 minutes at ambient temperature. (A range of 15-45 minutes is also useful.) The plate was drained and washed gently by flooding with PBS. After standing a few minutes, it was drained. The wash procedure was repeated three times.

The plate was then covered for 30 minutes (a range of 15-45 minutes being useful) at ambient temperature with the following bridging antibody: Rabbit anti-goat $I_gG$ (H&L) diluted to approximately 4-5%. This is used in excess to ensure that one antigen-binding site remains free to bind to the labeled antibody described below. The plate was washed gently as described in the previous paragraph.

The plate was then covered with the following labeled antibody:

Goat peroxidase—anti-peroxidase diluted to a concentration between 40 ug/ml. (A range of 25-50 ug/ml is useful.) The plate was incubated 30 minutes at ambient temperature, followed by a gentle washing as described in the previous paragraph. (An incubation time of 15-30 minutes is useful.)

The preceding steps were all preparatory to applying the overlay element of Example 5. That overlay was applied and the sandwich incubated at 37° C. for about five minutes. (Ambient temperature can also be used.) Thereafter, the overlay showed bands indicative of the peroxidase label, in room light. The smallest concentration of enzyme detected was eight nanograms of protein/microliter.

EXAMPLE 7

Detection of Creatine Kinase (CK) and Lactate Dehydrogenase (LD) in Cells

Cells were obtained from rats by the following procedure:

1. In Vivo Protocol
   a. Day 0: Rats were give 10 mL of tryptose phosphate broth (TPB) by i.p. injection—5 rats.
   b. Day 1:
   1) The same rats were give 10 mL of minimal essential medium (MEM) with heparin by i.p. injection.
   2) The belly area was quickly massaged and an 18 or 20 gauge needle and a 20 mL syringe was used to remove dislodged peritoneal macrophage cells.

2. In Vitro Protocol
   1) The fluid in the syringe was transferred to a 15 mL conical tube and placed in an ice bath.
   2) Peritoneal macrophages were harvested from remaining animals and placed into separate tubes.
   3) The tubes were centrifuged for 10 minutes at 1000-1500 rpm in a refrigerated centrifuge.
   4) Supernatants were removed and the pellets remaining were added to 10 mL of MEM with serum and heparin.
   5) The viable cells were counted to insure a yield of about $1-2 \times 10^6$ cells/rat.
   6) Between $7.5-8 \times 10^4$ cells suspended in MEM+10% cold fetal bovine serum (FBS) were placed onto sterile tissue-culture clean slides.
   7) The slides containing cells were then incubated at 37° C. in five percent $CO_2$ humidified incubator.

The following overlays were prepared:

CK Overlay

An overlay was prepared identical to that described for Example 1 above.

LD Overlay

The following overlay was prepared:

| | |
|---|---|
| Gelatin (hardened) | 5-20 g/m2 |
| Triton X-100 surfactant | 0.01-5 g/m² |
| Ottasept (preservative) | .001-.03 g/m² |
| N-tris (hydroxymethyl) methyl-2-aminoethane sulfonic acid (buffer) | 0.5-4.5 g/m² |
| NADH | 0.1-0.8 g/m² |
| Na Pyruvate | 0.05-0.25 g/m² |
| Bis(vinylsulfonylmethyl) ether (hardener) | 0.05-2.0 g/m² |
| Polyvinyl pyrrolidone K-90 | 0.1-2.0 g/m² |
| Support | |

The overlays were cut to fit the glass slides prepared as described above. The slides with the cells on them (invisible to the eye) were overlaid with first the LD overlay, and incubated in petri dishes containing wet filter paper for about 10 minutes at 37° C., to prevent the overlayed cells from drying out. After the overlay was removed, tell-tale bright patches were present when viewed under fluorescent light at 340 nm, indicating the enzyme was present in the cells.

Thereafter, the same slides plus cells were overlaid with the CK web, and the incubation repeated for ten minutes. Examination of the overlay under room light revealed blue patches, establishing that that enzyme was present and had leaked out of the cells.

EXAMPLE 8

Detection of Alkaline Phosphotase in Cells

The procedure of Example 7 was repeated, using the same overlay.

Incubation of the overlay on the cells on the slide occurred for ten minutes at 37° C. The color thereafter observed in the overlay was the tell-tale yellow indicative of alkaline phosphotase present in the cells.

The invention has been described in detail with particular reference to preferred embodiments thereof, but it will be understood that variations and modifications can be effected within the spirit and scope of the invention.

What is claimed is:

1. A method for determining an analyte, said method comprising the steps of:
   A. forming a temporary laminate by overlaying a plate adapted for electrically induced migration and containing a plurality of analytes which have been electrically separated from one another, with a dry, transparent analytical element containing a water-insoluble binder material having pre-dispersed therein a reactive component which will react with at least one of said analytes to form a non-diffusible, detectable species solely in said element, and
   B. removing said analytical element from said plate and detecting said detectable species in said analytical element.

2. The method of claim 1 wherein said analytes are proteins.

3. The method of claim 1 wherein said interactive composition reacts to provide a non-diffusible chromogen.

4. The method of claim 1 wherein after step A and prior to step B, said plate-element laminate is incubated at a temperature up to about 45° C. for a time sufficient for said analyte to be detected to react with said reactive component to generate a visible representation of the analyte.

5. A method for determining an analyte in an aqueous liquid, said method comprising the steps of:
   A. contacting an electrophoretic plate with a sample of said liquid,
   B. electrically separating a plurality of analytes from one another in said plate,
   C. forming a temporary laminate by overlaying said plate with a dry, transparent analytical element containing a water-insoluble binder material having predispersed therein an reactive component which will react with at least one of said analytes to form a non-diffusible, detectable species solely in said element, and
   D. removing said element from said plate and detecting said detectable species in said element.

6. The method of claim 5 wherein said reactive component reacts to provide a non-diffusible chromogen.

7. The method of claim 5 wherein said plurality of analytes are proteins or nucleic acids.

8. The method of claim 5 wherein said plurality of analytes are isoenzymes or enzymes.

9. The method of claim 8 wherein said plurality of isoenzymes are isoenzymes of creatine kinase, alkaline phosphotase or lactate dehydrogenase.

10. The method of claim 5 wherein said dry analytical element comprises a support having thereon at least one layer containing said binder material and said reactive component.

11. A method for detecting a plurality, (N), of analytes, said method comprising the steps of:
   A. forming a temporary laminate by overlaying a plate adapted for electrically induced migration and containing said plurality of analytes which have been separated from one another electrically, with a first analytical element containing a water-insoluble binder material having pre-dispersed therein a reactive component which will react with the first of said analytes while laminated to provide a first detectable species solely in said first element,
   B. removing said first element from said plate and
   C. repeating steps A and B up to N-1 times, using in each repetition of steps A and B, said plate and a respectively different dry analytical element containing a water-insoluble binder material having pre-dispersed therein a respective reactive component which will react with the respective analyte while laminated to form a respective detectable species solely in said respectively different element, provided that said reactive components of at least the first (N-1) detections react with said respective analytes to provide respective non-diffusible detectable species,
   and wherein each of said analytical elements is provided as a dry, transparent element.

12. The method of claim 11 wherein said plurality of analytes are proteins or nucleic acids.

13. The method of claim 12 wherein said plurality of proteins are enzymes or isoenzymes.

14. The method of claim 11 wherein after each performance of step A and before each performance of step B, said respective plate-element laminate is incubated at a temperature of up to about 45° C. and for a time sufficient for said respective analyte to react with said respective reactive component to generate a visible representation of the analytes, and each of said elements is essentially transparent.

15. A method for the determination of creatine kinase isoenzymes, said method comprising the steps of:
   A. forming a temporary laminate by overlaying an electrophoretic plate which contains said isoenzymes which have been electrically separated from one another with a dry, transparent analytical element,
   said element comprising before said Step A, a nonporous support having thereon, in order and in fluid contact, a first reagent layer containing peroxidase, a-glycerophosphate oxidase and a leuco dye which is capable of providing a non-diffusible detectable dye in response to said isoenzymes solely in said element, and a second reagent layer containing a water-insoluble binder material having dispersed therein creatine phosphate, adenosine diphosphate, glycerol and glycerol kinase, and
   B. removing said element from said plate and examining said element to determine said detectable dye in said element.

16. The method of claim 15 wherein said electrophoretic plate is composed of agarose, polyacrylamide or acrylamide.

17. The method of claim 15 wherein said water-insoluble binder material is hardened gelatin.

18. A diagnostic kit for the determination of an analyte, said kit comprising:
   a plate adapted for electrically induced migration of said analyte, and
   a dry transparent analytical element comprising a water-insoluble binder material having pre-dispersed therein a reactive component which is capable of reacting with said analyte to form a non-diffusible detectable species solely in said element.

19. The kit of claim 18 wherein said element comprises a nonporous support having thereon a reagent layer comprising said binder material and said reactive component.

20. The kit of claim 18 wherein said reactive component is capable of reacting with said analyte to provide a non-diffusible chromogen.

21. A method for determining an analyte in an aqueous liquid, said method comprising the steps of:
   A. contacting an electrophoretic plate with a sample of said liquid;
   B. electrically separating a plurality of analytes from one another in said plate;
   C. before or after Step B, adding an enzyme to said plate containing the analytes, in a form that selectively binds the enzyme to one of said analytes;
   D. forming a laminate by overlaying said plate with a dry transparent analytical element comprising a binder and a reactive component predispersed in said binder which will react with at least said enzyme to provide a non-diffusible, detectable species solely in said element; and
   E. removing said element from said plate and detecting said detectable species in said element.

22. The method of claim 21, wherein said enzyme is bound to an antibody specific to said analyte or to an antibody to said analyte.

23. The method of claim 21, wherein said Step C occurs after said Step B.

24. The method of claim 10 wherein said element comprises at least a detection layer and a layer separate from said detection layer comprising an enzyme substrate, on said support.

25. A method for the detection of intracellular enzymes in live cells, comprising
   disposing such cells on a support,
   and overlaying the support with a dry, transparent element comprising a water-insoluble binder and a reactive component pre-dispersed in said binder and capable of reacting with at least one of said enzymes to produce a detectable change.
   said reactive component further including a surfactant of the type and in an amount effective to induce leakage of said at least one enzyme out of the cells.

26. A method as defined in claim 25, wherein the enzyme is creatine kinase and said surfactant is selected from the group consisting of a sodium salt of an alkylaryl polyether sulfonate and sodium alkyl naphthalene sulfonate.

27. A method as defined in claim 25, wherein the enzyme is alkaline phosphotase and said surfactant is an octylphenoxy polyethoxy ethanol.

28. A method as defined in claim 25, wherein the enzyme is lactate dehydrogenase and said surfactant is an octylphenoxy polyethoxy ethanol.

* * * * *